United States Patent
Rudolph et al.

(10) Patent No.: US 10,130,826 B2
(45) Date of Patent: Nov. 20, 2018

(54) DEVICE AND A METHOD FOR TREATING A PATHOLOGY-AFFECTED SITE IN A SUBJECT

(71) Applicant: Wetling Holding APS, Hundested (DK)

(72) Inventors: Matthias Rudolph, Hong Kong (HK); John F. Wetling, Hundested (DK); Carsten Semark, Alleroed (DK); Arne Jensen, Roskilde (DK); Anders Bang Olsen, Bagsvaerd (DK)

(73) Assignee: Wetling IP LT LTD, Tortola (VG)

( * ) Notice: Subject to any disclaimer, the term of this patent is extended or adjusted under 35 U.S.C. 154(b) by 251 days.

(21) Appl. No.: 15/027,746

(22) PCT Filed: Oct. 7, 2014

(86) PCT No.: PCT/EP2014/071415
§ 371 (c)(1),
(2) Date: Apr. 7, 2016

(87) PCT Pub. No.: WO2015/052170
PCT Pub. Date: Apr. 16, 2015

(65) Prior Publication Data
US 2016/0236003 A1 Aug. 18, 2016

(30) Foreign Application Priority Data
Oct. 7, 2013 (DK) .................................. 2013 70556

(51) Int. Cl.
*A61N 1/44* (2006.01)
*A61N 5/06* (2006.01)
(Continued)

(52) U.S. Cl.
CPC ............. *A61N 1/44* (2013.01); *A61N 5/0613* (2013.01); *G21K 5/00* (2013.01);
(Continued)

(58) Field of Classification Search
None
See application file for complete search history.

(56) References Cited

U.S. PATENT DOCUMENTS 6,436,127 B1 8/2002 Anderson et al.
8,728,135 B2 * 5/2014 Shaffer .................... A61N 5/06
128/898
(Continued)

FOREIGN PATENT DOCUMENTS

WO WO-2007/042029 A1 4/2007
WO WO-2008/076986 A1 6/2008

OTHER PUBLICATIONS

International Search Report PCT/ISA/210 for International Application No. PCT/EP2014/071415 dated Mar. 10, 2015.
(Continued)

*Primary Examiner* — Brian T Gedeon
(74) *Attorney, Agent, or Firm* — Harness, Dickey & Pierce, P.L.C.

(57) ABSTRACT

A device for treating a pathology-affected site in a subject is disclosed. A first generator is configured for generating a first flux of ionized gas molecules, a second generator is operable simultaneously with the first generator and configured for generating a second flux of electromagnetic radiation. To ensure correct treatment, monitoring, documentation and enhanced analysis of the treatment, the device has computerized control means configured to be operable simultaneously with the first and second generators and configured to determine a net electrical charge of the subject while the first generator generates the first flux of ionized gas molecules and while the second generator generates the second flux of electromagnetic radiation. Also a client server computer network including the device is disclosed.

19 Claims, 7 Drawing Sheets

(51) Int. Cl.
G21K 5/00 (2006.01)
A61B 18/00 (2006.01)
(52) U.S. Cl.
CPC .............. *A61B 2018/00791* (2013.01); *A61N 2005/0627* (2013.01); *A61N 2005/0651* (2013.01); *A61N 2005/0659* (2013.01); *A61N 2005/0661* (2013.01); *A61N 2005/0662* (2013.01); *A61N 2005/0663* (2013.01)

(56) References Cited

U.S. PATENT DOCUMENTS

| | | | |
|---|---|---|---|
| 9,852,262 B2* | 12/2017 | Lampo | .................. G06F 19/324 |
| 2003/0045916 A1 | 3/2003 | Anderson et al. | |
| 2004/0116918 A1* | 6/2004 | Konesky | .............. A61B 18/042 |
| | | | 606/34 |
| 2005/0209660 A1* | 9/2005 | James | ...................... A61N 1/40 |
| | | | 607/100 |
| 2006/0071178 A1 | 4/2006 | Wetling | |
| 2006/0085053 A1 | 4/2006 | Anderson et al. | |
| 2010/0145253 A1 | 6/2010 | Gutsol et al. | |
| 2011/0112522 A1 | 5/2011 | Wetling | |
| 2012/0150044 A1 | 6/2012 | Kim | |
| 2013/0310731 A1 | 11/2013 | Gutsol et al. | |

OTHER PUBLICATIONS

Written Opinion of the International Searching Authority PCT/ISA/237 for International Application No. PCT/EP2014/071415 dated Mar. 10, 2015.
International Preliminary Report on Patentability PCT/IPEA/409 for International Application No. PCT/EP2014/071415 Dated Jan. 20, 2016.
Invitation to Pay Additional Fees PCT/ISA/206 for International Application No. PCT/EP2014/071415 Dated Dec. 12, 2014.

* cited by examiner

DEVICE AND A METHOD FOR TREATING A PATHOLOGY-AFFECTED SITE IN A SUBJECT

CROSS-REFERENCE TO RELATED APPLICATIONS

This application is the National Phase under 35 U.S.C. § 371 of PCT International Application No. PCT/EP2014/071415, which has an International filing date of Oct. 7, 2014, which claims priority to Danish Application Number PA 2013 70556, filed on Oct. 7, 2013; the entire contents of each of which are hereby incorporated by reference.

INTRODUCTION

The present invention relates to a treatment device for treating a pathology-affected site in a subject. Particularly, the invention relates to a device comprising a first generator means configured for generating a first flux of ionized gas molecules, and optionally a second generator means being operable simultaneously with the first generator means and configured for generating a second flux of electromagnetic radiation.

BACKGROUND OF THE INVENTION

Electrical stimulation (also termed electro stimulation or ES) is a well-known technology, which has been used in treatment of a large number of pathologies—when used in disease treatment, ES is often termed electrotherapy.

In practice ES involves the transfer of electric current through an applied surface electrode pad that is in electrolytic contact with the external skin surface and the area to receive the effect. In ES, at least two electrodes (a lead and a discharge electrode) are required to complete the electric circuit.

Using electrodes when ES treating a human or an animal includes the drawbacks that it is difficult i.a. due to manipulation of the electrodes, to control administration of the charge, and the treatment is known to be painful for the patients. In certain modes of ES (e.g. when using ES in wound treatment), there is also the added risk of infection because ES in such a context is an invasive method.

The literature about ES has increased exponentially in recent years. About 95 percent positively reports about the treatment despite an extraordinarily wide selection of experimental techniques and models. Fourteen research groups report that electrical currents stimulated fracture healing with few if any complications in a total of 595 patients. The mechanisms of action and ideal technique for applying stimulation have yet to be determined.

Nevertheless, ES has been used as a therapeutic means in a number of conditions, notably in the treatment of various types of wounds, such as acute wounds, burns, chronic wounds including pressure ulcers, diabetic ulcers, venous ulcers, and arterial ulcers.

It is an object of the present invention to improve the known devices and to facilitate an increased perception of the treatment. It is a further object to enable better control of the treatment, ability to monitor the treatment, and allow for documentation of the treatment and the effect thereof.

DESCRIPTION OF THE INVENTION

In a first aspect the present invention provides a device with computerized control means configured to be operable simultaneously with the first and optionally simultaneously with the second generators and configured to determine a net electrical charge of the subject while the first generator generates the first flux of ionised gas molecules and optionally while the second generator generates the second flux of electromagnetic radiation.

Since the computerized control means is operable simultaneously with the first and/or second generator means, it is possible to control the treatment and to collect data during the treatment, and particularly, it is possible to improve combined treatment with charged ions and electromagnetic radiation.

It has been found that the combination of electromagnetic radiation and ionized gas molecules increases the effect of traditional treatment with ionized gas molecules. According to the present invention, the device can offer such a combined treatment. According to the invention, the computerized control means is configured to determine the net charge while the first or while both the first and second generators are operating. Accordingly, the device according to the invention can determine the net charge not only resulting from the ionized gas molecules but also from the second flux of electromagnetic radiation. This enables data recording, monitoring of the treatment, documentation and control of the device based on the net electrical charge resulting from both the first and second flux. As a result, improved treatment, monitoring and documentation may be obtained.

The subject may be a mammal such as a human being or an animal.

The ionized gas molecules may be generated with both positive and negative electrical charge. However, it may be an advantage to neutralise the positively charged ionized gas molecules and only to direct the negatively charged ionized gas molecules towards the object. In one embodiment, the positively charged ionized gas molecules are generated and transmitted towards the object.

In one embodiment the generated ionized gas molecules may be directed in a first predetermined direction, e.g. towards the pathology-affected site. The device may comprise a transmitting structure configured to release the ionized gas molecules and to focus the molecules specifically in this direction. The transmitting structure could be provided with a variable spreading of the ionized gas molecules. The transmitting structure may comprise one or more transmitters, e.g. in the form of one or more antennas of an electrically conductive material.

The device may also comprise magnetic means for generating a magnetic field for controlling the direction of the ionized gas molecules which are released from the transmitting structure. The device may include control means for controlling such a magnetic field.

In one embodiment a substantial part of the gas molecules are directed in the predetermined direction towards the subject such as at least 30 percent of the ions, such as at least 50 percent of the ions, such as 70 percent of the ions.

The voltage output of the ionized gas molecules generator may be between 0 and 40.000 V, such as between 0 and 12.000 V, such as between 0 and 6.000 v, such as 1.500 volts, or 3.000 volts or 4.500 volts. Furthermore, the current output may be between 0 and 50 µA, such as between 0 and 25 µA, such as between 0 and 10 µA, such as between 0 and 5 µA, such as between 0 and 1 µA, such as between 0.05 and 3 µA, such as between 1 and 3 µA.

In one embodiment, the transmitting structure is adapted to transmit the ionized gas molecules trough air, so that a larger surface area of the treated object can be influenced by the ionized gas molecules simultaneously. In particular, the transmitting structure could be adapted to spread the ionized gas molecules over an area which increases with a factor 2 for each 10 cm increase in the distance between the treated object and the transmitting structure. It has been found that such gas molecules when conducted in free air from the transmitting structure towards the object may improve the treatment over the traditionally known methods implying direct contact between the transmitting structure and a surface of the treated object.

In one embodiment, the generated second flux of electromagnetic radiation is directed in a second predetermined direction, e.g. towards the pathology-affected site. The device may comprise an emitting structure for this purpose. The emitting structure may include at least one radiation emitting element such as two, three, four, five or ten radiation emitting elements. The radiation emitting elements may be adapted to emit the second flux in the predetermined direction and it may be adjustable such that the focal point can be changed, i.e. such that the second flux can be focused at variable distance from the device.

The emitting elements may comprise individual generators for generating the second flux, or it may be a release structure for releasing the second flux which is generated at another location. As an example, the second generator means may comprise one single centralised generator and the second flux can be distributed, e.g. by use of fibre optics, to one or more emitting elements, or alternatively, each emitting element may comprise an individual generator thereby forming part of the second generator means. The emitting elements may also include one or more optic lenses for focusing the second flux at one or more points.

When several emitting elements exist, they may be configured to emit the second flux with identical intensity and at identical wavelengths. Alternatively, the radiation emitting elements are chosen such that they emit radiation at different wavelengths and/or intensities.

In one embodiment, the transmitting structure and the emitting structure are movable relative to each other, or they are at least adjustable individually such that the first and second predetermined directions can be varied individually.

The device according to the present invention may comprise a pointing device for generating at least one beam of visible light. The pointing device may particularly be operatively associated with at least one of the transmitting structure and the emitting structure such that its beam or beams of light indicates at least one of the first and second predetermined directions. This will enable adjustment of the transmitting and emitting structures to ensure exposure of the pathology affected site.

The second generator may particularly be configured to generate ultra-violet radiation, visible light, micro waves or similar radio waves and/or infrared radiation. Accordingly, the electromagnetic radiation may have wavelengths in the range of $10^4$ and $10^{-9}$ meters, such as in the range of $10^{-8}$ and $10^{-3}$ meters, such as in the range of 400 nm and 700 nm, or particularly within a wavelength in the range of 185-380 nm.

The electromagnetic radiation intensity may be in the range of 0 and 100.000 Lumens, such as between 100 and 10.000 Lumens, such as between 1.000 and 5.000 Lumens. Furthermore, in one embodiment of the invention the second generator may be configured to deliver the radiation at an intensity whereby the pathology-affected site can be treated with up to 10.000 Lux, such as between 100 and 5.000 Lux, such as between 500 and 1.000 Lux. In one embodiment, the device comprises one or several light emitting diodes (LEDs). In particular such LEDs may each constitute the second generator and one of the mentioned emitting elements in one combined unit. The LEDs may be arranged peripherally around the transmitting structure.

The electromagnetic radiation could be generated by a heat lamp, e.g. a water filtered heat lamp. The treatment may thereby include heating of the skin surface of the subject to a certain temperature by use of the combination between light and ions.

The ionized gas molecules are carrying an electrical charge which is transferred to the treated subject. To determine the net electrical charge, the device may comprise a first connecting structure for establishing electrical connection between the subject and the feedback structure. Furthermore, it may comprise a second connecting structure for establishing electrical connection between the transmitting structure and the feedback structure. In that way, a closed loop is established from the transmitting structure, through the air to the surface of the subject, along a surface of the subject or through the body of the subject to the first connecting structure, through the first connecting structure to a feedback structure and from the feedback structure to the transmitting structure. The feedback structure may include an ampere meter which determines an electrical current through a body portion of the subject.

For the purpose of ensuring correct monitoring, for documentation, and/or for allowing exchange of knowledge e.g. to include expert opinions from abroad, the computerised control means may include storage capacity for data storage and it may be configured to record treatment data which represents a treatment.

Herein, the term computerized control means may particularly encompass a CPU with associated ram, power supply, data storage and communication means for communicating data with a user and/or with the first and second generators and/or with other devices, e.g. devices of the same kind, or with image and/or sound capturing and/or recording devices.

The computerized control means may become capable of establishing user profiles and capable of recording treatment data by having predefined profiles and predefined treatment data which can be selected, or may become capable of establishing user profiles and capable of recording treatment data by having predefined schemes which can be filled out by the user, e.g. one predefined scheme for the subject which is treated, another predefined scheme for the staff using the device, another predefined scheme for defining experts, and/or predefined schemes for filling out treatment data.

The computerised control means may particularly be capable of establishing a user profile for at least one of the following three groups of users:

the subjects which are treated by the device;
the staff using the device; and/or
the experts which can gain online or off-line access to data from the device.

Herein subject is the person being treated by the device, staff is the person(s) facilitating the treatment by use of the device i.e. typically the medical practitioner, and experts are other persons gaining access to data from the device. The term "user" includes all three groups, i.e. the subjects, the staff, and the experts.

For each group of users, the profile may identify the user and it may further contain data identifying e.g. the time and date of each interaction between the device and the user in question.

In one embodiment, the computerized control means is configured to record consumption data which represents how much electrical energy is consumed by the device. This may apply during one treatment, during several treatments for the same subject, during treatments with the same staff, or during treatments in total during a certain period in time, e.g. during the lifetime of the device or since the latest service or inspection of the device. The consumption data may be included in the treatment data and it may be added to the user profile.

In one example, the treatment data contains indication of the total duration of treatment for a specific patient, or a total amount of charged particles being used, e.g. expressed in coulomb.

In one embodiment, the computerized control means may be configured to count a number of treatments carried out. This may apply as a number of single treatments carried out on different subjects, it may apply as a number of treatments carried out on the same subject, during treatments with the same staff, or during treatments in total during a certain period in time, e.g. during the lifetime of the device or since the latest service or inspection of the device. The count of treatments may be included in the treatment data and it may be added to the user profile.

In one embodiment, the computerized control means may be configured to record a temperature of the skin surface of the subject being treated. This recording may apply during one treatment, during several treatments for the same subject, during treatments with the same staff, or during treatments in total during a certain period in time, e.g. during the lifetime of the device or since the latest service or inspection of the device. The temperature may be added to the user profile. In one embodiment, the computerized control means may be configured to control the first and second generator means based on the recorded temperature, e.g. to stop treatment when a threshold temperature is reached. The device may include wired or wireless temperature recording means, e.g. in the form of a infra-red camera temperature sensor.

In one embodiment, the computerized control means is configured to record a duration in which the device has been active. This may apply during one treatment, during several treatments for the same subject, during treatments with the same staff, or during treatments in total during a certain period in time, e.g. during the lifetime of the device or since the latest service or inspection of the device. The recorded duration may be included in the treatment data and it may be added to the user profile.

In one embodiment, the computerized control means is configured to summarize the net electrical charge of the subject. This may apply during one treatment, during several treatments for the same subject, during treatments with the same staff, or during treatments in total during a certain period in time, e.g. during the lifetime of the device or since the latest service or inspection of the device. The summarized net electrical charge may be included in the treatment data and it may be added to the user profile e.g. in a measurable unit which is comparable with a reference measure such that the treatment can be evaluated based on that measure. In one example, the measured unit is coulomb.

The device may further comprise image recording means configured to record image data representing the reflected electromagnetic radiation. The image recording means may include a one array ccd-camera, a matrix ccd-camera or any other means for capturing image data. The image data may particularly represent a reflection of the second flux of electromagnetic radiation from the surface of the subject.

Particularly, the image recording means configured to record image data representing the reflected electromagnetic radiation in the infrared wavelength to thereby determine a skin surface temperature of the treated subject. In that way, the image recording means may function as a temperature sensor.

For separating the reflection of the second flux of electromagnetic radiation from other electromagnetic radiation, e.g. from the light of other light sources in the environment, the device may include filters and software known in the art. In the following, we refer to captured data representing data captured by the image recording means and enhanced reflection data representing data which is obtained by filtering methods to represent particularly the reflection of the second flux of electromagnetic radiation from the surface of the subject.

The computerized control means may be configured to adjust at least one of the first and second fluxes and/or to control the net electrical charge.

As an example, the computerized control means may be configured to stop at least one of the first and the second generator means and thereby to stop the treatment automatically based on a specific condition, e.g. based on a net electrical charge through the subject, an intensity of reflected electromagnetic radiation reflected from the subject etc., or the computerized control means may be configured to reduce the flux from at least one of the first and the second generator means and thereby to reduce the net electrical charge based on a specific condition.

As an example, the computerized control means may be configured to stop the treatment after a specific duration of the treatment, after a certain Coulomb value, i.e. quantity transferred by one ampere in one second. As an example, the device may stop after 1-2 minutes, or after 5-10 minutes, or after 30-90 minutes or whichever time interval or quantity of electricity is suitable for a specific subject.

The computerized control means may be configured to adjust the dose of at least one of the ionized gas molecules and/or the electromagnetic radiation. The dose may be adjusted based on the net electrical charge, and the adjustment may be carried out by changing settings for the first and/or the second generator and/or by changing the distance between the pathology-affected site and the emitter and transmitter, respectively.

Particularly the computerized control means may be configured to adjust at least one of the first and second fluxes and/or to control the net electrical charge based on the image data. As an example, the adjustment may be based on the intensity or wavelength or spectrum of the reflection of the second flux of electromagnetic radiation from the surface of the subject.

For the purpose of adjusting the flux or net electrical charge, the computerized control means may be configured to provide operational data representing variable settings or readings of the device during treatment, e.g. operational data which includes at least one of a field strength of the first flux, a field strength of the second flux, a duration in which at least one of the first and the second flux is aimed at the site, and an electrical charge through the subject. Accordingly, the computerized may obtain actual settings and parameters which are relevant for the treatment.

The computerized control means may be configured to provide from the image data, at least one image parameter representing at least one of an intensity and a wave length of the reflected electromagnetic radiation. The computerized control means may be configured to adjust at least one of the first and second fluxes based on a difference between the second flux and the reflected electromagnetic radiation.

The computerized control means may be configured to record sets of operational data linked to corresponding image data. This may apply for one specific treatment of a specific subject, it may apply for several treatments for the same subject, for treatments with the same staff, or for treatments in total during a certain period in time, e.g. during the lifetime of the device or since the latest service or inspection of the device. The recorded sets of operational data may be included in the treatment data and it may be added to the user profile.

In one embodiment, the computerized control means may adjust at least one of the first and second fluxes based on a combination between the image data and the net current through the subject.

In one embodiment, the computerized control means constitutes a client in a client server computer network in which a server communicates data with a plurality of computerized control means of corresponding other devices of the same kind. In such a system, the mentioned operational data and treatment data may be stored in a storage which can be accessed by all clients, or which can be accessed by at least one client or the server. In one embodiment, one computer system has access to the two data sets and is configured to carry out analysis of at least one of the data sets to provide an enhanced set of data representing operational data and/or treatment data for all clients of the client server network, herein the enhanced set of data is referred to as treatment identification data.

The device according to the invention may include pre-defined terms for expressing predetermined conditions, parameters, treatments, and results of the treatment, e.g. ion current, light intensity, light color, image sampling interval, actual ion current, actual light intensity, ambient temperature, body surface temperature.

The device may further comprise a support structure for supporting the subject, e.g. during treatment. In order to provide predetermined and predictable operating conditions, the support structure may comprise an insulation structure for electrically isolation of the subject from ambient space. The insulating structure may be provided as an insulating surface, e.g. the surface of an examination couch on which the subject is supported. Alternatively, or as a supplement, legs of the couch or similar supporting structure may comprise the insulating structure. The insulating structure may be provided as an insulating layer on a couch or it may be implemented in a suspension or stand of the couch. The insulation of the subject during treatment enables measuring of an electrical current through the subject during the treatment.

In a second aspect, the invention provides such a client server computer network comprising a server and a plurality of clients in data communication with the server, each client being constituted by computerized control means of devices of the kind described herein.

The system may be configured to communicate the treatment data and/or the operational data related to variable settings of each of the clients. The server may be configured to process the data to provide treatment identification data based on data from all clients. The treatment identifier could e.g. be an ID number or other unique identifier.

The network may be configured to communicate data related to a number of treatments, a duration in which the device has been active, a summarized net electrical charge of the subject, image data representing reflected electromagnetic radiation, image parameters representing at least one of an intensity and a wave length of the reflected electromagnetic radiation, or operational data representing variable settings or readings of the device during treatment.

In a third aspect, the invention provides a method of treating a pathology-affected site in a subject with a first flux of ionized gas molecules and a second flux of electromagnetic radiation, the method comprising the steps of:
locating the object in a support structure which is electrically isolated from ambient space,
exposing the object to the first and second flux,
while image data representing electromagnetic radiation from the pathology-affected site is recorded during treatment.

Particularly, data related to a plurality of sites and related to a number of treatments, a duration in which the device has been active, a summarized net electrical charge of the subject, image data representing reflected electromagnetic radiation, image parameters representing at least one of an intensity and a wave length of the reflected electromagnetic radiation, or operational data representing variable settings or readings of the device during treatment may be communicated to a server computer system where the data is processed to provide a treatment identifier based on the data.

Particularly, the method may be directed to non-medical purpose, e.g. for enhancing the wellbeing of a person or animal or for pure esthetic reasons, e.g. for changing the skin color of a human being or animal.

The invention according to the second and third aspects of the invention may comprise any feature or element mentioned relative to the first aspect of the invention.

DETAILED DESCRIPTION OF THE DRAWINGS

It should be understood that the detailed description and specific examples, while indicating embodiments of the invention, are given by way of illustration only, since various changes and modifications within the spirit and scope of the invention will become apparent to those skilled in the art from the detailed description.

Figure 1:
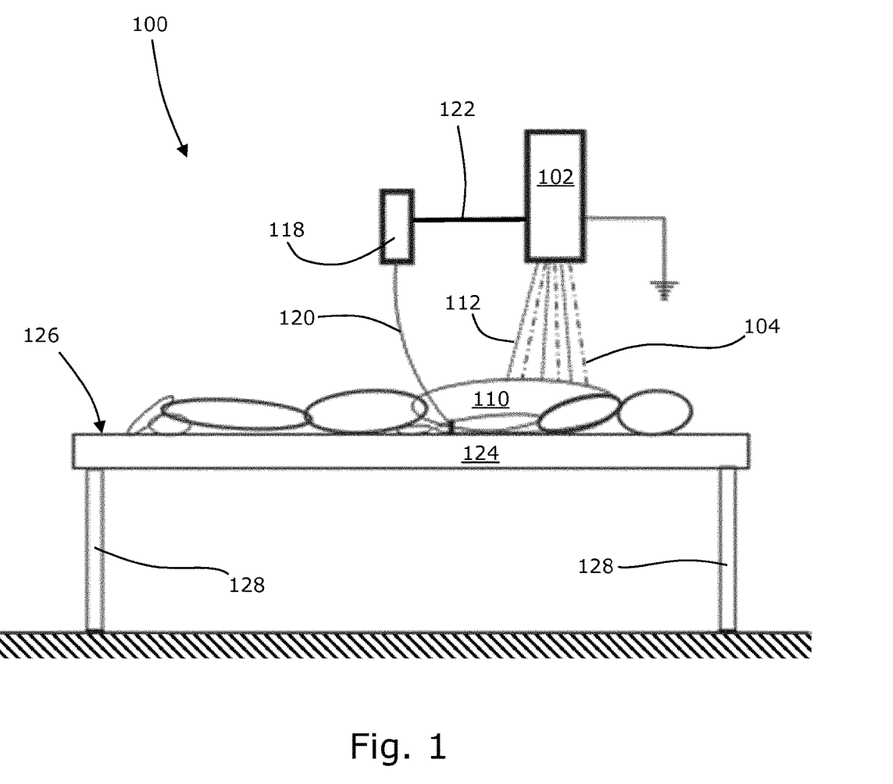
FIG. 1 discloses an arrangement comprising an air-gas molecule transmitting device according to the present invention, FIG. 2 discloses a unit comprising an air-gas molecule transmitting structure and radiation emitting elements.

FIG. 1 discloses a device 100 for treating a subject. The device 100 comprises a unit 102 comprising an ionized gas molecule generator connected to an ionized gas molecule transmitting structure for directing a part of the ionized gas molecules in a predetermined direction. The flow of ionized gas molecules is indicated by dash-dotted line 104, which thus indicates the predetermined direction. The ionized gas molecule transmitting structure comprises a transmitting surface 106, as may be seen in FIG. 2 in which the unit 102 is seen from below. Furthermore, the unit 102 comprises three radiation emitting elements 108 which are adapted to emit electromagnetic radiation towards the subject 110 as indicated by dotted lines 112 in FIG. 1. In the embodiment of the figures, the radiation emitting elements 108 comprises conventional light bulbs which thereby constitute the second generator means according to the invention.

Figure 2:
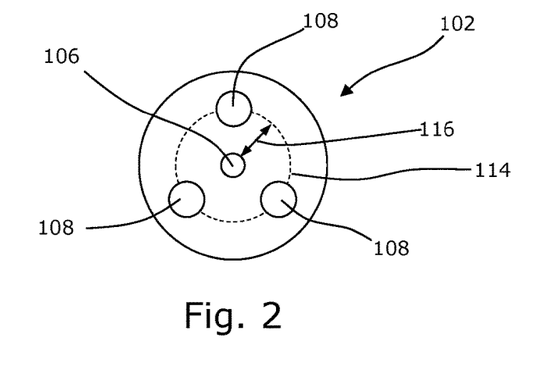

As it may be seen in FIG. 2 the radiation transmitting elements are arranged on a circle indicated by dashed line 114, such that the distance 116 between the ionized gas molecule transmitting surface 106 and each of the radiation emitting elements 108 is identical. Furthermore, the radiation emitting elements 108 are movable such that the distance 116 may be changed. The subject is connected to a feedback structure 118 by means of a first connecting structure 120. In the figure the first connecting structure 120 is connected to the wrist of the object. Furthermore, the feedback structure 118 is connected to the ionized gas molecule generator via a second connecting structure 122. Due to the first connecting structure 120 the feedback structure 118 may measure a dose of at least one of the ionized gas molecules and/or the electromagnetic radiation received by the subject 110. This information may be used to control the ionized gas molecule generator by means of the second connecting structure 122, such that the received ions/radiation is at a predetermined level. During treatment the subject 110 is located on a support structure 124 which is insulated from ambient space as it comprises an insulating layer, which may be provided on a surface 126 of the support structure 124 or forms part of one of the legs 128. In general, the object should be electrically isolated from the ambience by any means, e.g. by use of legs or leg parts made of an insulating material, e.g. rubber legs under the couch, by use of an insulating layer between the couch and the legs, between the legs and the floor or by an electrically insulating sheet between the object and the couch or by hanging the couch on a wall or from the sealing by use of an insulating suspension.

Figure 3:
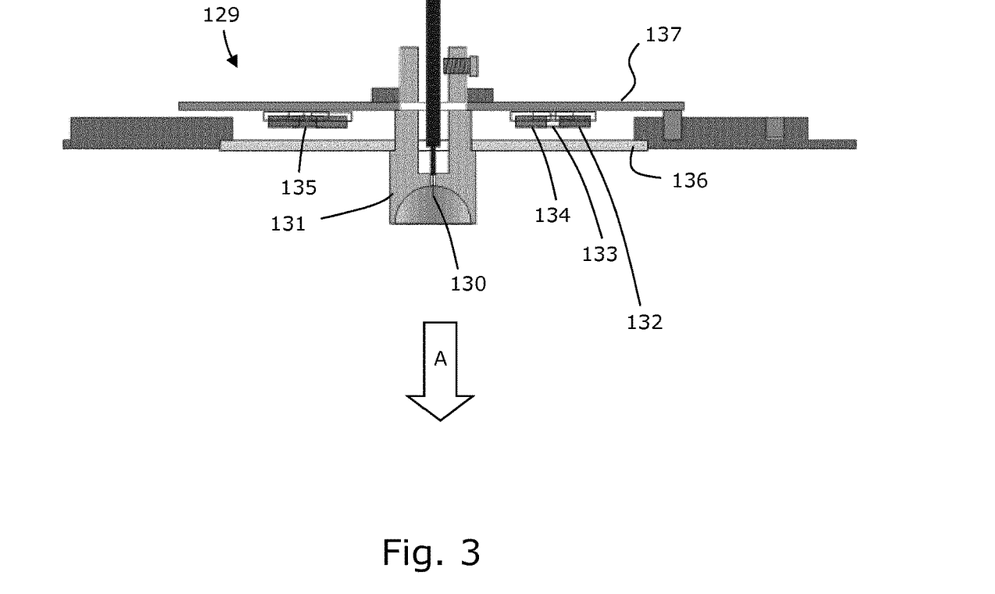
FIG. 3 illustrates in a cross sectional view, one embodiment of a device.
Figure 4:
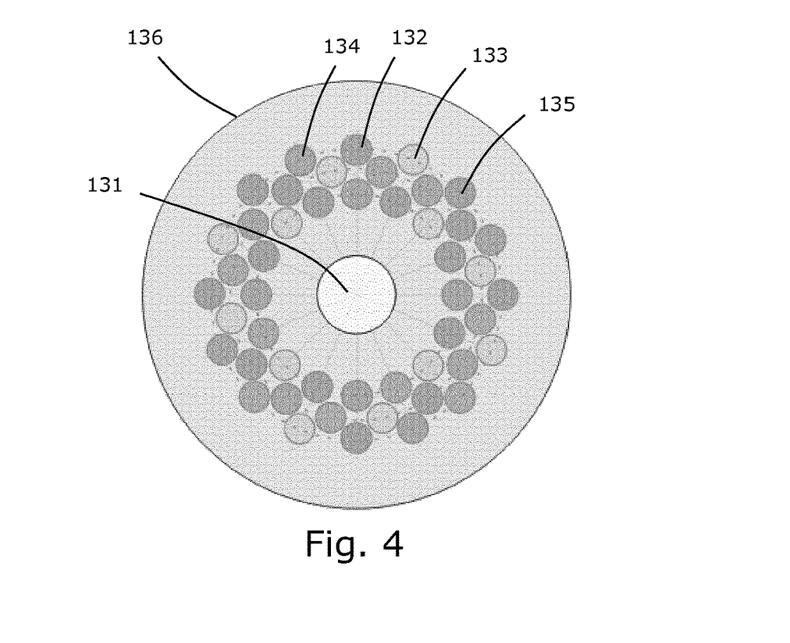
FIG. 4 illustrates a top view of the device shown in FIG. 3.

FIG. 3 illustrates an air-gas molecule treatment device 129. The device comprises an ionized gas molecule generator for generating a dose of ionized gas molecules. The ionized gas molecules are transmitted from the transmitting structure 130 which is located in the shield 131. In addition, the device comprises a plurality of red LEDs 132, yellow LEDs, 133 and green LEDs 134 and blue LEDS 135. The LEDs are located behind a mirror 136 which allows light from the LED to pass through the mirror in the downward direction indicated by the arrow A. The LEDs are all joined by a printed circuit board 137. As indicated more clearly in FIG. 4, the LEDs are arranged circumferentially around the ionized gas molecule transmitting part of the device. In another embodiment, all or at least some of the LEDs or alternative light sources are adapted to transmit white light, and specific colours are generated by use of coloured glass between the object and the light source. Any other kind of light sources could be used.

Figure 5:
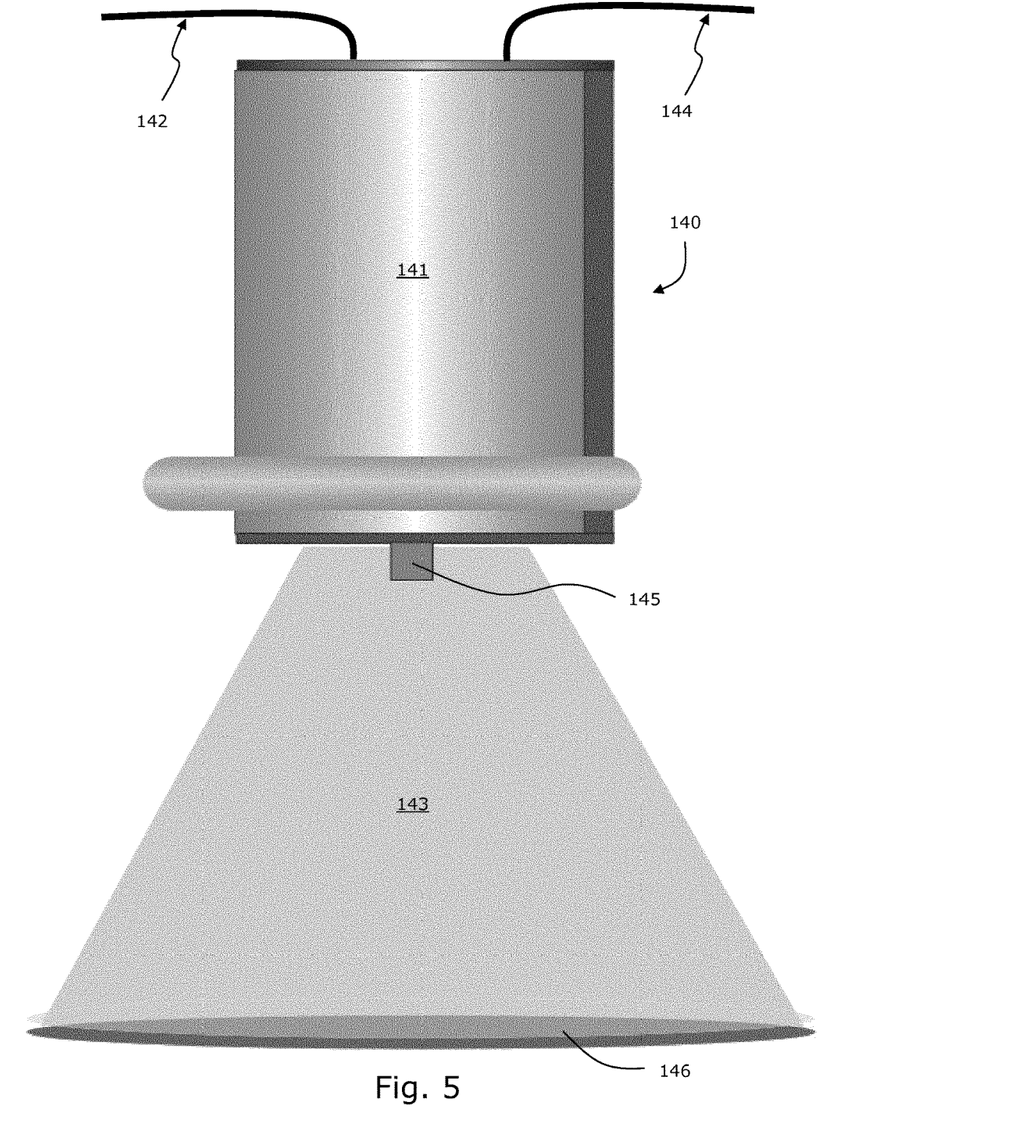
FIG. 5 illustrates a device in a side view.

FIG. 5 illustrates a device 140 seen from one side. The device comprises a housing 141 in which the ionized gas molecules are generated and in which the lamps which generate electromagnetic radiation are located. The device is provided with electrical power via the power cord 142. As indicated by the grey zone 143, the ionized gas molecules and the light are transmitted in a transmission zone downwardly onto the object which is treated.

The connecting structure 144 electrically connects the device to a port where the charge carried by the gas molecules to the object can be collected, so the electrical current through the body, or along a surface of the body of the treated object, can be measured. The ionized gas molecules are transmitted from the transmitting structure 145. A relatively large area, indicated by the grey area 146, on the surface of the treated object is exposed to the electrically ionized gas molecules and electromagnetic radiation.

In the following, an example of a treatment is described:

A patient is placed on the support structure with the chest upwards and with a bare upper body. The unit is positioned 25 cm from the upper body of the patient. The device is set to transfer 1.5 µA for a period of 10 minutes. The radiation emitting device is set to emit radiation during the 10 minutes. After the 10 minutes the device is turned off automatically. The total transfer of electrical charge is 900 coulomb. Hereafter the patient is turned around such that the chest faces downwards and the process is repeated.

Alternatively, the current output could be between 0 and 50 µA, such as between 0 and 25 µA, such as between 0 and 10 µA, such as between 0 and 5 µA, such as between 0 and 1 µA, such as between 0.05 and 3 µA, such as between 1 and 3 µA.

The following two examples are to illustrate an observed effect of the treatment when carried out on two different objects.

To control the patients, a well-known method (Prognos from the German company MedPrewent) has been used for measuring the electrical resistance in the meridians in the body.

Patient A

Figure 6:
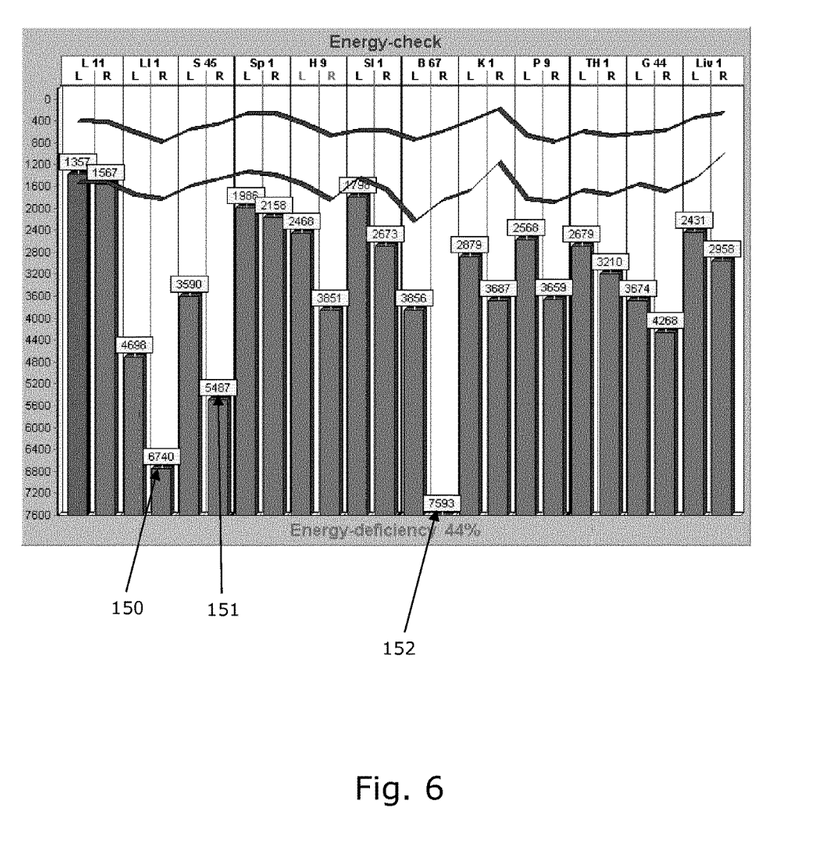
FIGS. 6-9 illustrate various results of measurements conducted on treated objects.

FIG. 6 illustrates the result of a measuring of a 53 years old female suffering of pain in her shoulders and in the lover part of her spinal. According to the patient, the pain is most of the time concentrated in her right side.

According to the result of the measuring is can be seen that the highest resistant is in the right side at the meridians for the large intestine, c.f. numeral 150, the stomach, c.f. numeral 151, and the urine bladder, c.f. numeral 152 This is a very good indication that the patient in fact does has the pain which she has asked to be relieved of.

Figure 7:
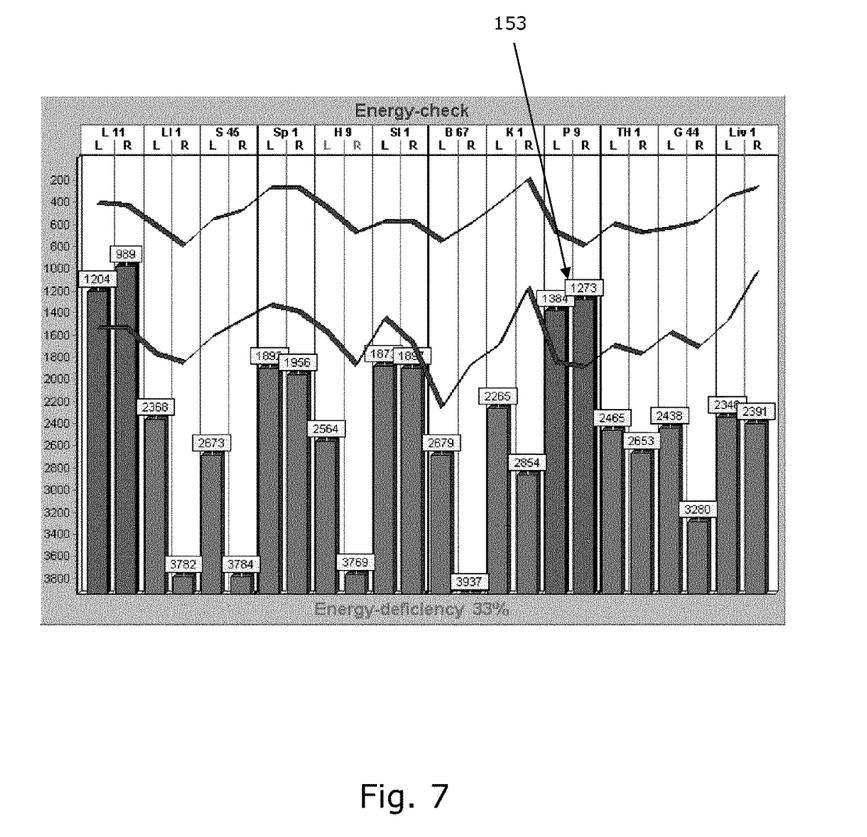

FIG. 7 illustrates the results of a measurement after three times with a treatment with the device according to the present invention. The patient tells that the pain is reduced considerably.

The measurements illustrates that the resistance in the meridians has changed to the better. The resistance in three meridians in focus after the first control has been reduced by the treatment, and the patient confirms that the pain has been reduced. A very good result is also to be seen at the meridian for the circulation, c.f. FIG. 7 numeral 153.

Patient B

A young professional sportsman 22 years old having some pain in his knee and his common condition is not sufficient to keep him on the first team. He is asking for help with both problems.

Figure 8:
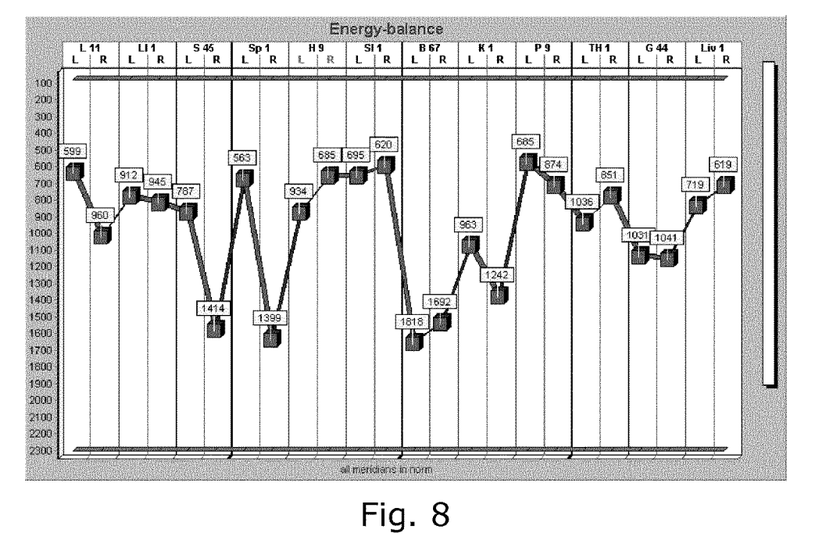

The control measuring illustrated in FIG. 8 shows a too large unbalance, and both of the above-mentioned problems are considered to relate to this unbalance.

Figure 9:
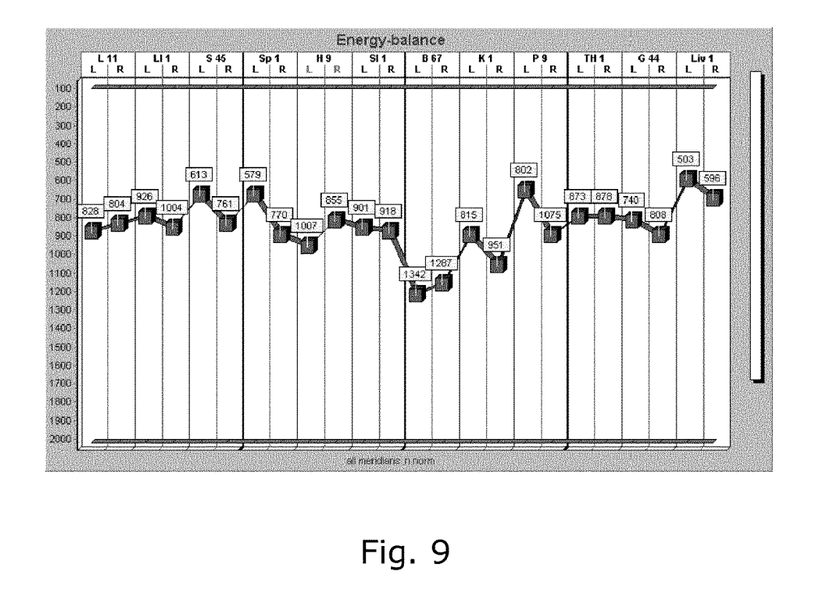

A control measuring after the fifth treatment, c.f. FIG. 9, shows a much higher balance between the meridians, and combined with explanations obtained from the patients about the condition when the treatment was finished.

Figure 10:
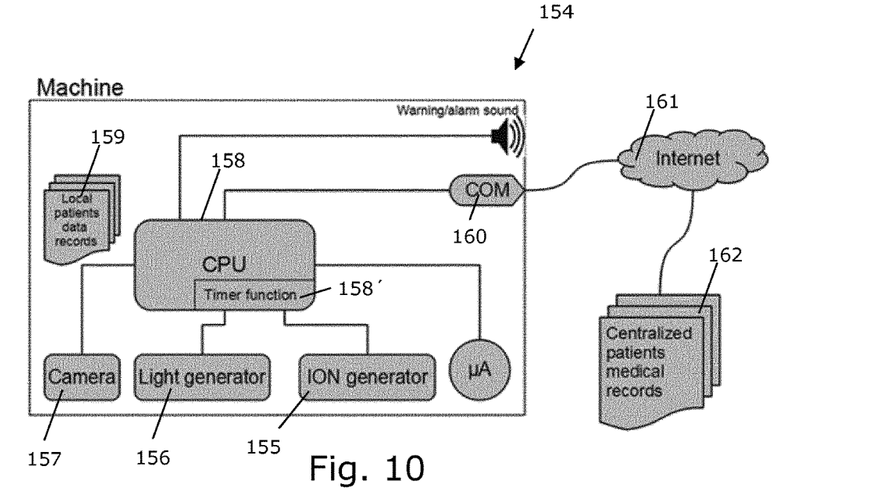
FIG. 10 is a diagramatic representation of a device according to the invention.

FIG. 10 illustrates a diagramatic representation of a device according to the invention. The device 154 comprises a first generator means 155 which is configured for generating a first flux of ionized gas molecules. The device comprises a second generator means 156 which can generate a second flux of electromagnetic radiation. In this embodiment, the second generator means 156 is a lamp which emits light. The device further comprises an image recording means 157 configured to record image data representing the reflected electromagnetic radiation. In the illustrated embodiment, the image recording means is a camera which can take snapshots and/or video sequences. The Camera could be a HUCam-HUV09 from Huentek Co. Ltd???

The device 154 further comprises a computerized control means which is operable simultaneously with the first and second generators. The computerized control means is embedded in a CPU board 158. The first generator is controlled and regulated by a real time current measurements circuit. The current circuit is connected to the subject with a wire and the current through the subject can hereby be measured and controlled, so the living object will get a constant current. The range of the constant current from the first generator can be set in the device by the staff. The machine provides a warning sound if a constant current setup cannot be achieved within a specifically set distance to the subject. If the constant current setup cannot be achieved, the device must be adjusted and moved closer to the subject until the setup first generator current can be achieved.

The computerized control means comprises a computerized timer by which the device can be controlled. The timer 158' can be set and adjusted by the staff. The first generator will run until the timer expires for each treatment setup. The timer can be set by the staff to achieve the best treatment result for the given treatment type. The treatment functions (first and second generators) can be timer controlled and the staff can set up a treatment where the treatment continues until the timer expires. The timer can be set by the staff to achieve the best treatment result for the given treatment type.

The device comprises a COM interface 160 enabling communication with external computer systems. The device may e.g. be connected to the Internet 161 and thereby form a client server treatment system together with other similar devices and a server. The client server treatment system may include a database 162 comprising treatment date or operational data. I.e. treatment results and treatment procedures are saved in the centralized patient database.

In a local database 159, treatment schedules, treatment procedures, and treatment results can be stored. The treatment results are documented by use of the camera and the data may further comprise counted coulomb and current measurements.

The machine can be built as a portable machine with all functions integrated.

In practise, the machine may include several different PCB boards:

LED PCB board: The board is mounted with LEDs in difference wave length from 380 nm to 860 nm. The LED board is controlled by the computerized PCB board which constitutes the core in the computerised control means.

ION generator PCB board: The ION generator for generating the ionized gas molecules. The ION generator is controlled by the computerized PCB board.

Camera PCB board: A camera integrated in the machine for record of treatment results.

Computerized PCB board: The computerized board is designed with a CPU, memory, power supply for the other PCB boards, Internet connection, timer function, warning sound and interfaces to all PCB boards in the machine.

The computerized board is controlling the LED, ION generator and the camera boards. The computerized board has a local memory for saving of patient treatment results locally. The computerized board has an Internet connection.

Power supply: The machine is powered with a power supply connected to the public electric grid or to an electric battery source.

Software: Software in the machine is constructed in a way where the operator easily can select the wanted treatment procedure.

The software for the CPU on the computerized board is constructed by use of low level software codes. The software for the centralized patient database is constructed by use of standard web and standard database high level development tool.

Mechanical: The machine is built as a portable or stationary machine with all functions integrated. The machine can be constructed with a head where ION generator, light generator and computerized board are mounted. The machine can be constructed with a multi direction adjustable arm/stand for best and stable positioning setting.

Figure 11:
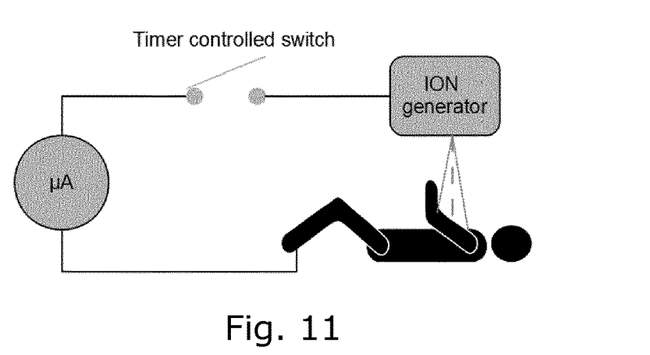
FIGS. 11 and 12, illustrate treatment of a human being placed horizontally on a treatment couch.
Figure 12:
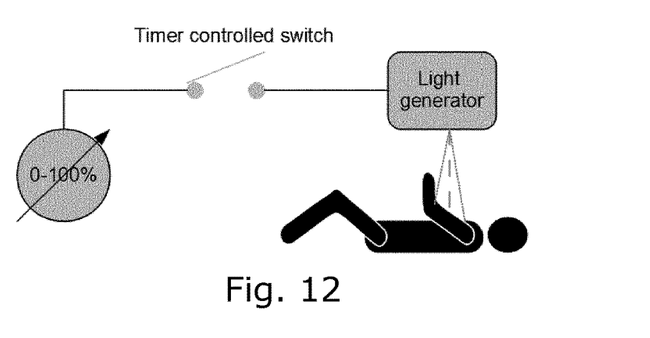

The machine can be used for treatment of e.g. a human being placed horizontally on a treatment couch, c.f. FIGS. 11 and 12. The head of the machine must be focused over the wanted treatment area. The operator can then setup the wanted treatment procedure and then initiate the treatment.

The invention claimed is:

1. A device for treating a pathology-affected site in a subject, the device comprising:
   a first generator configured to generate a first flux of ionized gas molecules;
   a second generator configured to operate simultaneously with the first generator and further configured to generate a second flux of electromagnetic radiation;
   a computing device configured to operate simultaneously with the first and second generators and further configured to determine a net electrical charge of the subject concurrently with the first generator generating the first flux of ionized gas molecules and the second generator generating the second flux of electromagnetic radiation;
   an image recording device configured to record image data representing reflected electromagnetic radiation; and
   a feedback structure configured to determine an electrical current through the subject,
   where the computing device is further configured to adjust at least one flux of the first flux or the second flux based on a combination between the image data and the electrical current through the subject.

2. A device according to claim 1, wherein the computing device includes storage capacity for data storage, and the computing device is configured to record treatment data which represents a treatment of a subject.

3. A device according to claim 1, where the computing device is configured to record consumption data which represents how much electrical energy is consumed by the device during one treatment, during several treatments for a specific subject or in total during a certain period in time.

4. A device according to claim 1, where the computing device is configured to count a number of treatments carried out by use of the device.

5. A device according to claim 1, where the computing device is configured to record a duration in which the device has been active.

6. A device according to claim 1, where the computing device is configured to summarize the net electrical charge of the subject.

7. A device according to claim 1, where the computing device is configured to adjust at least one flux of the first flux and the second flux based on the image data.

8. A device according to claim 1, where the computing device is configured to provide from the image data, at least one image parameter representing at least one of an intensity and a wave length of the reflected electromagnetic radiation.

9. A device according to claim 1, wherein the computing device is configured to provide operational data representing variable settings or readings of the device during treatment.

10. A device according to claim 9, where the operational data includes at least one of a field strength of the first flux, a field strength of the second flux, a duration in which at least one of the first and the second flux is aimed at the pathology-affected site, and an electrical charge through the subject.

11. A device according to claim 1, where the computing device is configured to adjust at least one of the first and second fluxes based on a difference between the second flux and the reflected electromagnetic radiation.

12. A device according to claim 9, where the computing device is configured to record sets of operational data linked to corresponding image data.

13. A device according to claim 1, where the second generator is configured to generate electromagnetic radiation with a wavelength in a range of 185-380 nm.

14. A device according to claim 1, where the computing device constitutes a client in a client server computer network in which a server communicates data with a plurality of computing device of corresponding other devices.

15. A client server computer network comprising a server and a plurality of clients in data communication with the server, each client being constituted by computing devices of devices according to claim 1.

16. A client server computer network according to claim 15, configured to communicate data related to variable settings of each of the clients, and where the server is configured to process the data to provide treatment identification data based on data from all clients.

17. A client server computer network according to claim 15, configured to communicate data related to a number of treatments, a duration in which the device has been active, a summarized net electrical charge of the subject, image data representing reflected electromagnetic radiation, image parameters representing at least one of an intensity and a wave length of the reflected electromagnetic radiation, or operational data representing variable settings or readings of the device during treatment.

18. A method of treating a pathology-affected site in a subject with a first flux of ionized gas molecules, the method comprising:
locating an object in a support structure which is electrically isolated from ambient space,
simultaneously exposing the object to the first flux of ionized gas molecules and to a second flux of electromagnetic radiation and recording image data representing electromagnetic radiation from the pathology-affected site;
determining a net electrical charge of the subject concurrently with the exposure of the object to the first flux of ionized gas molecules and the second flux of electromagnetic radiation;
determining an electrical current through the subject; and
adjusting at least one flux of the first flux or the second flux based on a combination between the image data and the electrical current through the subject.

19. A method according to claim 18, where data related to a plurality of sites and related to a number of treatments, a duration in which a device has been active, a summarized net electrical charge of the subject, image data representing reflected electromagnetic radiation, image parameters representing at least one of an intensity and a wave length of the reflected electromagnetic radiation, or operational data representing variable settings or readings of the device during treatment is communicated to a server computer system where the data is processed to provide a treatment identifier based on the data.

* * * * *